United States Patent
Hsieh

(10) Patent No.: US 10,610,190 B2
(45) Date of Patent: Apr. 7, 2020

(54) PORTABLE MEDICAL DEVICE AND METHOD OF CONTROLLING PORTABLE MEDICAL DEVICE

(71) Applicant: Samsung Electronics Co., Ltd., Gyeonggi-do (KR)

(72) Inventor: Jong-jyh Hsieh, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 260 days.

(21) Appl. No.: 15/729,764

(22) Filed: Oct. 11, 2017

(65) Prior Publication Data

US 2018/0110494 A1    Apr. 26, 2018

(30) Foreign Application Priority Data

Oct. 26, 2016    (KR) .................. 10-2016-0140175

(51) Int. Cl.
| | | |
|---|---|---|
| *A61B 6/00* | (2006.01) | |
| *A61B 6/10* | (2006.01) | |
| *H04N 7/18* | (2006.01) | |
| *G08G 9/02* | (2006.01) | |

(Continued)

(52) U.S. Cl.
CPC .............. *A61B 6/547* (2013.01); *A61B 6/035* (2013.01); *A61B 6/102* (2013.01); *A61B 6/4405* (2013.01);

(Continued)

(58) Field of Classification Search
CPC ..................................................... A61B 6/547

(Continued)

(56) References Cited

U.S. PATENT DOCUMENTS

| 4,181,347 A | 1/1980 | Clark |
|---|---|---|
| 4,449,746 A | 5/1984 | Clark |

(Continued)

FOREIGN PATENT DOCUMENTS

| JP | 2009-534737 A | 9/2009 |
|---|---|---|
| KR | 10-2016-0020462 A | 2/2016 |
| KR | 10-2016-0049291 A | 5/2016 |

OTHER PUBLICATIONS

Korean Search Report dated Oct. 24, 2017.

*Primary Examiner* — Eileen M Adams
*Assistant Examiner* — Daniel T Tekle
(74) *Attorney, Agent, or Firm* — Cha & Reiter, LLC.

(57) ABSTRACT

Provided is a portable medical device including a drive motor configured to provide power to move the portable medical device; at least one camera configured to capture an image of a periphery of the portable medical device; an ultrasonic sensor configured to emit an ultrasonic signal to the periphery of the portable medical device and detect the ultrasonic signal reflected from a first obstacle located in the periphery of the portable medical device; a torque sensor configured to detect a torque value of the drive motor; a processor configured to generate information about the first obstacle based on the image captured by the at least one camera and/or the detected ultrasonic signal and calculate an expected movement path of the portable medical device based on the torque value detected by the torque sensor; and a display configured to display a periphery image using the image captured by the at least one camera, the information about the first obstacle, and the expected movement path of the portable medical device.

18 Claims, 12 Drawing Sheets

(51) Int. Cl.
*A61B 6/03* (2006.01)
*H04N 5/247* (2006.01)
*H04N 5/445* (2011.01)
*H04N 5/232* (2006.01)
*G06T 7/50* (2017.01)
*G06T 7/20* (2017.01)
*H04N 5/44* (2011.01)

(52) U.S. Cl.
CPC ............... *G08G 9/02* (2013.01); *H04N 5/247* (2013.01); *H04N 5/445* (2013.01); *H04N 7/185* (2013.01); *G06T 7/20* (2013.01); *G06T 7/50* (2017.01); *G06T 2207/30241* (2013.01); *H04N 5/23293* (2013.01); *H04N 5/4403* (2013.01)

(58) Field of Classification Search
USPC .......................................................... 348/77
See application file for complete search history.

(56) References Cited

U.S. PATENT DOCUMENTS

| | | | |
|---|---|---|---|
| 7,397,895 | B2 | 7/2008 | Bailey et al. |
| 7,438,471 | B2 | 10/2008 | Tybinkowski et al. |
| 8,694,191 | B2 | 4/2014 | Van Den Berg |
| 8,770,839 | B2 | 7/2014 | Gregerson et al. |
| 9,731,717 | B2 | 8/2017 | Kim et al. |
| 9,766,072 | B2 | 9/2017 | Kim |
| 2010/0230183 | A1* | 9/2010 | Van Den Berg ....... A01K 1/105 180/6.48 |
| 2014/0258918 | A1 | 9/2014 | Morishima et al. |
| 2014/0372037 | A1* | 12/2014 | Kim ................... B62D 15/0295 701/541 |
| 2016/0114798 | A1* | 4/2016 | Kim ...................... B60W 30/09 701/41 |

* cited by examiner

PORTABLE MEDICAL DEVICE AND METHOD OF CONTROLLING PORTABLE MEDICAL DEVICE

CLAIM OF PRIORITY

This application claims the benefit of Korean Patent Application No. 10-2016-0140175, filed on Oct. 26, 2016, in the Korean Intellectual Property Office, the disclosure of which is incorporated herein in its entirety by reference.

BACKGROUND

1. Field

The present disclosure generally relates to a portable medical device, a method of controlling the portable medical device, and a non-transitory computer-readable recording medium having recorded thereon a program for executing the method.

2. Description of the Related Art

Medical devices have been developed to diagnose, detect, treat, and/or alleviate diseases or disorders of objects such as human bodies by diagnosing conditions of the objects or acquiring images of internal structures within the object. For example, in computer tomography (CT), X-rays are irradiated onto a body of a patient and images thereof are captured. CT devices are a type of medical imaging device or tomography device.

Recently, there has been an increase in the popularity of portable medical devices capable of performing diagnosis and medical treatment. These portable medical devices are small and light weight enough that they can be moved within a hospital from one operating room to another.

These portable medical devices may include wheels and motors and may be moved by the force of a user who pushes the portable medical device. Due to an increase in the number of portable medical devices, restrictions on places where these medical devices are used have been reduced and patient convenience has increased.

However, when moving the portable medical device, since the user's view is hindered by the portable medical device, there is a risk that the user and/or the portable medical device may be hit by an obstacle present on the moving path when moving the portable medical device.

SUMMARY

The present disclosure provides a portable medical device capable of preventing collision with an obstacle while the portable medical device is being moved and a method of controlling the portable medical device.

In addition, the present disclosure provides methods of giving users guidance on expected travel paths, safe travel paths, and the like, thereby enhancing user convenience.

Additional aspects will be set forth in part in the description which follows and, in part, will be apparent from the description, or may be learned by practice of the presented embodiments.

According to an aspect of an embodiment, a portable medical device includes a drive motor configured to provide power to move the portable medical device; at least one camera configured to capture an image of a periphery of the portable medical device; an ultrasonic sensor configured to emit an ultrasonic signal to the periphery of the portable medical device and detect the ultrasonic signal reflected from a first obstacle located in the periphery of the portable medical device; a torque sensor configured to detect a torque value of the drive motor; a processor configured to generate information about the first obstacle based on the image captured by the at least one camera and/or the detected ultrasonic signal and calculate an expected movement path of the portable medical device based on the torque value detected by the torque sensor; and a display configured to display a periphery image using the image captured by the at least one camera, the information about the first obstacle, and the expected movement path of the portable medical device.

The drive motor may include a left wheel drive motor and a right wheel drive motor, wherein the torque sensor is further configured to detect a torque value of the left wheel drive motor and a torque value of the right wheel drive motor, and wherein the processor is further configured to calculate a steering vector using the torque value of the left wheel drive motor and the torque value of the right wheel drive motor and calculate the expected movement path based on the steering vector.

The processor may be further configured to calculate a first number of revolutions of the left wheel drive motor and a second number of revolutions of the right wheel drive motor using position information of rotors inside the left wheel drive motor and the right wheel drive motor, compute a difference between the first number and the second number, and calculate the steering vector of the portable medical device based on the difference.

The display may be further configured to display the information about the first obstacle and the expected movement path on the periphery image.

The display may be further configured to display the expected movement path by using a reference line indicating a forward direction of the portable medical device and a direction line indicating an expected traveling direction of the portable medical device.

The processor may be further configured to set a safe movement path of the portable medical device for avoiding the first obstacle when the first obstacle is located within the expected movement path of the portable medical device, and wherein the display is further configured to display information about the safe movement path.

The processor may be further configured to control the portable medical device to automatically move along the safe movement path.

When the first obstacle is a moving obstacle, if a magnitude of an angle between a relative position vector, indicating a relative position between the portable medical device and the moving obstacle, and a relative velocity vector, indicating a relative velocity between the portable medical device and the moving obstacle, is between 0 and 90 degrees, the processor may be further configured to determine that collision between the portable medical device and the moving obstacle is not possible, and if the magnitude of the angle is between 90 and 180 degrees, and when a distance between the portable medical device and the moving obstacle is smaller than a sum of radiuses of the portable medical device and the moving obstacle, the processor may be further configured to determine that the collision between the portable medical device and the moving obstacle is possible.

The processor may be further configured to output an alarm notification when the first obstacle is located within a predetermined range from the portable medical device, and wherein the alarm notification includes at least one of a visual alarm, an audible alarm, and a tactile alarm.

The processor may be further configured to control the drive motor to decelerate or stop the portable medical device when a distance between the portable medical device and the first obstacle is smaller than or equal to a reference distance.

The at least one camera may include a first camera that captures images at a front of the portable medical device, a second camera that captures images at a right side of the portable medical device, and a third camera that captures images at a left side of the portable medical device, and wherein the processor is further configured to generate the periphery image by using images captured by the first, second, and third cameras.

The at least one camera may include a fourth camera directed upwards from the portable medical device, wherein the ultrasonic sensor includes an upper ultrasonic sensor configured to emit an ultrasonic signal upwards from the portable medical device and detect the ultrasonic signal reflected from a second obstacle located above the portable medical device, wherein the processor is further configured to detect the second obstacle o based on one or more images captured by the fourth camera and/or the ultrasonic signal detected by the upper ultrasonic sensor, and wherein the display is further configured to display information about the second obstacle.

The display may be further configured to enlarge and display a selected part of the periphery image according to a user input that selects the part of the periphery image.

The portable medical device may further include: a user inputter configured to receive a steering input from a user, wherein the processor is further configured to calculate the expected movement path of the portable medical device based on the steering input.

According to an aspect of another embodiment, a method of controlling a portable medical device includes capturing an image of a periphery of the portable medical device to generate a periphery image; emitting an ultrasonic signal to the periphery of the portable medical device; detecting the ultrasonic signal reflected from an obstacle located in the periphery of the portable medical device; detecting a torque value of a drive motor that provides power to move the portable medical device; generating information about the obstacle based on the captured image and/or the detected ultrasonic signal; calculating an expected movement path of the portable medical device based on the detected torque value; and displaying the periphery image, the information about the obstacle, and the expected movement path of the portable medical device.

The drive motor may include a left wheel drive motor and a right wheel drive motor, wherein the detecting of the torque value of the drive motor includes: detecting a torque value of the left wheel drive motor and a torque value of the right wheel drive motor, and wherein the calculating of the expected movement path of the portable medical device includes: calculating a steering vector using the torque value of the left wheel drive motor and the torque value of the right wheel drive motor and calculating the expected movement path based on the steering vector.

The calculating of the steering vector may include: calculating a first number of revolutions of the left wheel drive motor and a second number of revolutions of the right wheel drive motor using position information of rotors inside the left wheel drive motor and the right wheel drive motor, computing a difference between the first number and the second number, and calculating the steering vector of the portable medical device based on the difference.

The displaying of the expected movement path of the portable medical device may include: displaying the information about the obstacle and the expected movement path on the periphery image.

The method may further include: setting a safe movement path of the portable medical device for avoiding the obstacle when the obstacle is located within the expected movement path of the portable medical device; and displaying information about the safe movement path.

According to an aspect of another embodiment, a non-transitory computer-readable recording medium having recorded thereon a program for executing any of the above-mentioned methods is also provided.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
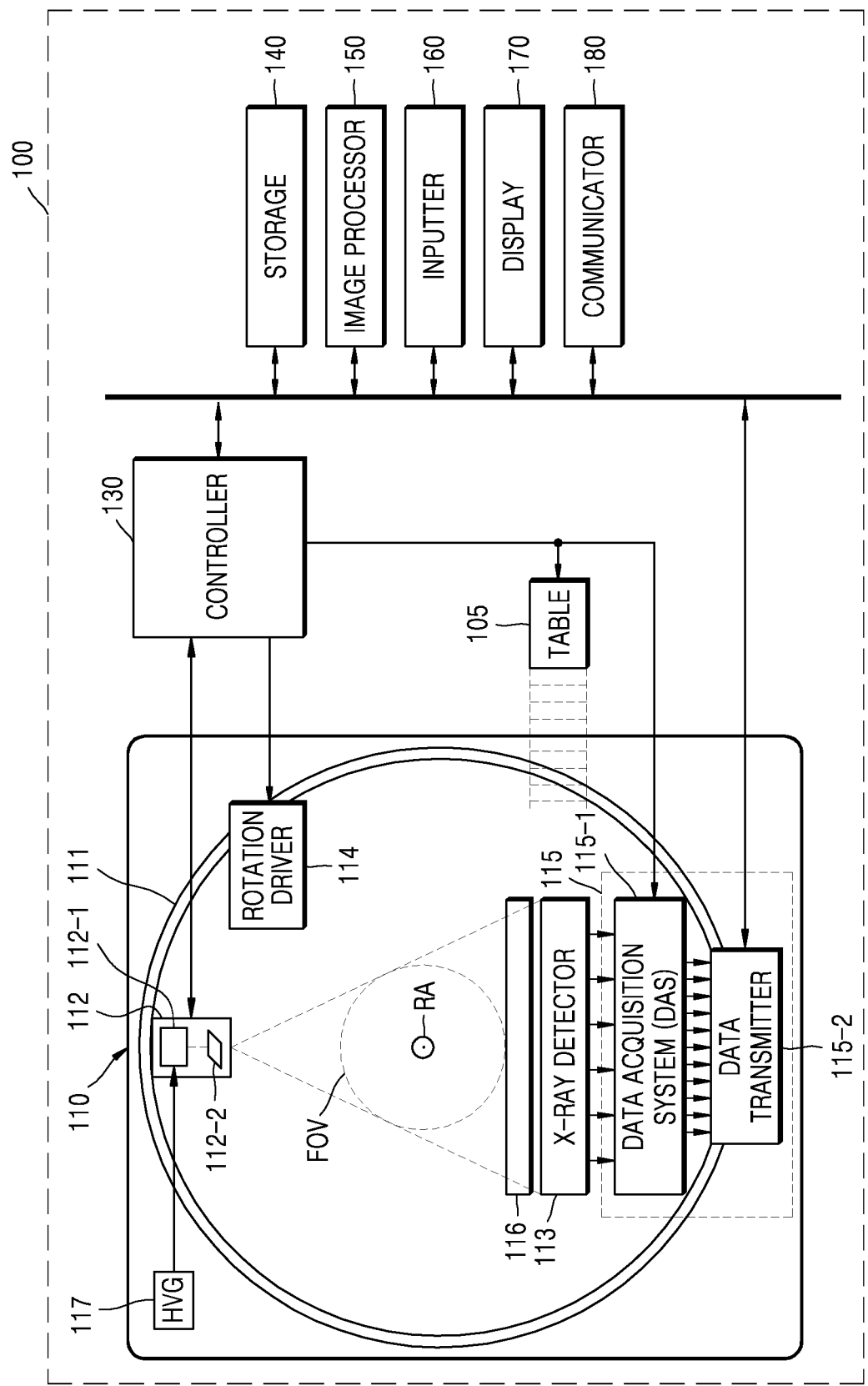
FIG. 1 is a block diagram illustrating structures of a computed tomography (CT) system according to an embodiment.

Reference will now be made in detail to embodiments, examples of which are illustrated in the accompanying drawings, wherein like reference numerals refer to like elements throughout. In this regard, embodiments may be different from those disclosed herein and therefore the present disclosure should not be construed as being limited to the descriptions set forth herein. Accordingly, the embodiments disclosed herein are for illustrative purposes only. Expressions such as "at least one of," when preceding a list of elements, modify the entire list of elements and do not modify the individual elements of the list.

The present specification clarifies the scope of the present disclosure, explains the principles of the present disclosure and discloses embodiments so that those skilled in the art may implement the present disclosure. The disclosed embodiments may be implemented in various forms, even those not disclosed herein, without departing from the spirit of the disclosure.

The present specification does not necessarily describe all the elements of the embodiments and omits redundant disclosures between embodiments where appropriate. As used in the present specification, parts and portions of the disclosed systems may be embodied in software and/or hardware. Plural terms such as "parts" and "portions" may be embodied in one "unit" or one "element." Conversely, one "part" and one "portion" may include a plurality of units or elements. Hereinafter, the operating principle and embodiments of the present disclosure will be described with reference to the accompanying drawings.

Herein, the disclosed images may be medical images obtained by medical imaging devices such as a computer tomography (CT) device, a magnetic resonance imaging (MRI) device, an ultrasound imaging device, an X-ray imaging device, etc.

As used herein, the term "object" may refer to a person, an animal, or a part thereof as an object whose images are captured by the medical imaging devices. For example, the object may include a part of the body, such as an organ, or phantom, and the like.

As used herein, the term "CT system" or "CT device" refers to a system or device that rotates in relation to at least one axis with respect to an object, irradiates X-rays, and detects the X-rays to capture images of the object.

In the present specification, the term "CT image" means an image composed of raw data obtained by the CT system.

FIG. 1 is a block diagram illustrating the structures of a computed tomography (CT) system 100 according to an embodiment.

The CT system 100 according to an embodiment may include a gantry 110, a table 105, a controller 130, a storage 140, an image processor 150, an inputter 160, a display 170, and a communicator 180.

The gantry 110 may include a rotation frame 111, an X-ray generator 112, an X-ray detector 113, a rotation driver 114, and a lead-out unit 115. The gantry 110 also includes a rotor that rotates in relation to an axis and a stator that supports the rotor.

The rotor may include the rotation frame 111, the X-ray generator 112, and the X-ray detector 113. The rotation frame 111 may rotate in relation to a predetermined rotation axis (RA), and may have, for example, a cylindrical shape or a ring shape. Under control of the controller 130, the rotation driver 114 induces or generates a driving force for rotating the rotation frame 111 using a motor or the like. The rotation of the rotation frame 111 allows the X-ray generator 112 and the X-ray detector 113 to rotate along a circumferential direction of the rotation frame 111. In addition, the rotor may include a slip ring that contacts the rotation frame 111 to transmit a signal or electric power, a bearing that reduces frictional force of the rotor, and the like.

The stator may support the rotor by using a housing, a station frame, a rotation shaft bearing, or the like.

The radiation reaching the X-ray detector 113 includes attenuated primary radiation that forms an image of the object and scattered radiation that degrades quality of the image. A scatter prevention grid 116 is disposed between the object and the X-ray detector 113 to improve image quality by primarily transmitting the main radiation and attenuating the scattered radiation.

The object is placed on a table 105. The table 105 may be moved, tilted, and rotated.

The X-ray generator 112 receives voltage and current from a power distribution unit (PDU) through the slip ring and a high voltage generator (HVG) 117 to generate and emit X-rays. The X-rays emitted from the X-ray generator 112 may have the form of, for example, a cone beam or a parallel beam, etc.

The X-ray generator 112 may be implemented by a single source method in which one X-ray generator 112 and one X-ray detector 113 are provided, or a dual source method in which two X-ray generators 112 and two X-ray detector 113 are provided.

The X-ray detector 113 detects the radiation that has passed through the object. The X-ray detector 113 may detect radiation using, for example, a scintillator, a photon counting detector, or the like.

The driving method of the X-ray generator 112 and the X-ray detector 113 may vary depending on scanning methods used for the object. Scanning methods include axial scanning method, helical scanning method, and the like, which may vary the movement path of the X-ray detector 113. In addition, the scanning method be in a prospective mode, a retrospective mode, and the like, which may vary the time period during which the X-ray is irradiated.

The controller 130 may control operations of each component of the CT system 100. The controller 130 may include a memory that stores program code and/or data for performing the control and a processor that processes the program code and the data. The controller 130 may be implemented in various combinations of one or more memories and one or more processors. The processor may create and delete program modules according to an operation state of the CT system 100 and may process operations of the program modules. The processor may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Aspects of the disclosure may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

The lead-out unit 115 receives the detection signal generated by the X-ray detector 113 and outputs the detection signal to the image processor 150. The lead-out unit 115 may include a data acquisition system (DAS) 115-1 and a data transmitter 115-2. The DAS 115-1 amplifies the signal output from the X-ray detector 113 using at least one amplifying circuit, and outputs the amplified signal to the data transmitter 115-2. The data transmitter 115-2 outputs the signal amplified by the DAS 115-1 to the image processor 150 using a circuit such as a multiplexer (MUX). When only slices of the images are required, only a part of data collected from the X-ray detector 113 may be provided to the image processor 150.

The image processor 150 generates tomography data from the signal (for example, raw data prior to processing) from the lead-out unit 115. The image processor 150 may perform preprocessing on the signal from the lead-out unit 115, conversion processing converting the signal into tomography data (e.g. reconstruction processing), and post-processing on the tomography data. The image processor 150 may perform some or all of processes described in the present disclosure. Types and order of the processes performed in the image processor 150 may vary in different embodiments.

The tomography data may have the form of filtered back-projection data, a tomography image, etc. According to embodiments, additional processing for the tomography data may be performed by an external device such as a server, a medical device, a portable device, or the like.

Raw data may be a collection of data values corresponding to intensity of X-rays that have passed through the object and may include projection data or a sinogram. The filtered back-projection data is data obtained by filtering and projecting back the raw data using information about angles at which the corresponding X-rays are radiated. The tomography image is an image obtained by applying reconstruction imaging techniques, which may include operations such as filtering and back-projecting the raw data.

The storage 140 is a storage medium that stores control related data, image data, and the like, and may include a volatile or nonvolatile storage medium.

The inputter 160 receives control signals, data, and the like from a user. The control signals may include, for example, a control signal for controlling a capturing operation of the CT system 100, a control signal for controlling display of medical images captured by the CT system 100, and the like.

The display 170 may display information indicating the operational state of the CT system 100, medical information, medical image data, and the like.

The CT system 100 includes the communicator 180 and may be connected to an external device (for example, a server, a medical device, a portable device (a smart phone, a tablet PC, a wearable device, etc.) through the communicator 180.

The communicator 180 may include one or more components that enable communication with the external device, and may include, for example, at least one of a short-range communication module, a wired communication module, and a wireless communication module.

The communicator 180 may receive control signal and data from the external device and may transmit the received control signal to the controller 130 so that the controller 130 controls the CT system 100 according to the received control signal. This way, a user may control the CT system 100 from the external device.

Similarly, the controller 130 may transmit the control signal to the external device through the communicator 180, thereby controlling the external device according to the control signal of the controller 130.

For example, the external device may process data according to the control signal of the controller 130 received through the communicator 180.

A program capable of controlling the CT system 100 may be installed in the external device, and may include instructions to perform some or all of the operations of the controller 130.

The program may be installed in the external device in advance, or may be downloaded from a server when a user of the external device is using the external device. The server providing the program may include a recording medium in which the program is stored.

The CT system 100 according to the embodiments may or may not require the use of a contrast agent for CT imaging.

Figure 2:
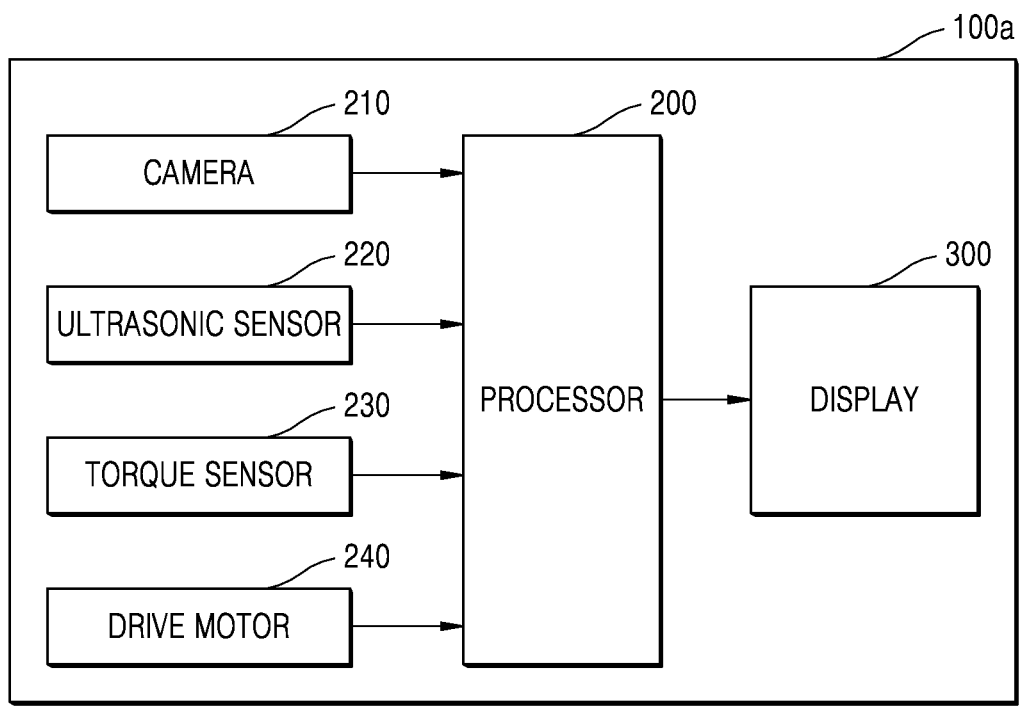
FIG. 2 is a block diagram illustrating structures of a portable medical device according to an embodiment.

FIG. 2 is a block diagram illustrating structures of a portable medical device 100a according to an embodiment.

The portable medical device 100a, which may be bulky and large, may determine whether there is an obstacle in its moving direction through images captured by a camera. The camera may be mounted at the front of the portable medical device 100a, such that it may capture images of the prospective moving direction. However, in such an arrangement blind spots at the periphery of the images may be common, and there is a risk of colliding with obstacles located in the blind spots. Accordingly, there is a need to detect obstacles located in the periphery of the portable medical device 100a as the portable medical device 100a is moved. The portable medical device 100a according to one or more disclosed embodiments displays the positions of the portable medical device 100a and obstacles in the moving path from a third person view point. Accordingly, obstacles in the periphery of the portable medical device 100a may be readily displayed to the user.

The portable medical device 100a according to an embodiment may include a plurality of cameras 210, an ultrasonic sensor 220, a torque sensor 230, a plurality of drive motors 240, a processor 200, and a display 300.

The portable medical device 100a may be implemented as a CT system, an MRI system, a digital radiography (DR) system, and the like. In other words, the portable medical device 100a may be implemented as any medical device that provides portability.

According to an embodiment, the camera 210 may capture the periphery of the portable medical device 100a. The camera 210 may include at least one camera, but preferably may include a plurality of cameras. For example, the camera 210 may include a camera mounted on the front of the portable medical device 100a to capture the path of the portable medical device 100a directly ahead and cameras that capture left side and right side of the portable medical device 100a.

According to an embodiment, the camera 210 may include a camera directed upwards that captures images above the portable medical device 100*a*. Such a camera may prevent the portable medical device 100*a* from colliding with obstacles located above the portable medical device 100*a*.

According to an embodiment, the camera 210 may include a camera mounted on the back of the portable medical device 100*a*. This way, the camera 210 may still capture the path of the portable medical device 100*a* when the moving direction of the portable medical device 100*a* is reversed.

Thus, according to an embodiment, the camera 210 may provide images of the periphery of the portable medical device 100*a*. The direction of image capture depends on where the camera 210 is mounted on the portable medical device 100*a*. For example, the camera 210 mounted on the front surface of the portable medical device 100*a* may acquire image information in the forward direction of the portable medical device 100*a*. Acquisition of images according to positions of the camera 210 will be described later in the other drawings.

According to an embodiment, the ultrasonic sensor 220 may emit an ultrasonic signal in the periphery of the portable medical device 100*a* and may detect the ultrasonic signal reflected from obstacles located in the periphery. Accordingly, the ultrasonic sensor 220 may detect the presence of the obstacles and measure distances between the obstacles and the portable medical device 100*a*.

The ultrasonic sensor 220 may be implemented as one or a plurality of sensors. At least one ultrasonic sensor 220 may be installed at a location on the portable medical device 100*a* corresponding to a location of at least one camera 210.

According to an embodiment, the torque sensor 230 may detect a torque value of the drive motor 240. For example, the torque sensor 230 may detect each of torque values of the drive motors 240 provided on the left and right sides of the portable medical device 100*a*. The torque sensor 230 may be independently provided for each of the plurality of drive motors 240. For example, the torque sensor 230 may include a torque sensor that detects a torque value of a left wheel drive motor and a torque sensor that detects a torque value of a right wheel drive motor.

According to an embodiment, the drive motor 240 may provide power to move the portable medical device 100*a*. The drive motor 240 may include the left wheel drive motor and the right wheel drive motor. The drive motor 240 may include a rotor.

According to an embodiment, the processor 200 may control the overall operation of the portable medical device 100*a* and process data generated by the camera 210, ultrasonic sensor 220 and torque sensor 230. The processor 200 may include at least one processor. According to an embodiment, the processor 200 may be as a processor that performs the operations of controlling the portable medical device 100*a*, including calculating an expected movement path of the portable medical device 100*a*.

The processor 200 may calculate the expected movement path of the portable medical device 100*a* based on the torque value detected by the torque sensor 230. The processor 200 may calculate a steering vector using the torque value of the left wheel drive motor and the torque value of the right wheel drive motor. The processor 200 may calculate the expected movement path based on the steering vector.

According to an embodiment, the processor 200 may generate a periphery image (e.g. images showing the periphery of the portable medical device 100*a*) using the images received from the camera 210. The generated periphery image may show an overlap of the obstacle and the expected movement path.

The processor 200 may combine images received from the plurality of cameras 210 to generate images of the periphery of the portable medical device 100*a* from a third person view point. For example, the processor 200 may generate an image looking at the portable medical device 100*a* from a bird's eye view.

The processor 200 may calculate the number of rotations of the left wheel drive motor and the right wheel drive motor using position information of the rotors in the left wheel drive motor and the right wheel drive motor. The processor 200 may calculate the steering vector of the portable medical device 100*a* by calculating a deviation between the number of rotations of the left wheel drive motor and the number of rotations of the right wheel drive motor.

According to an embodiment, when the obstacle is located in the expected movement path of the portable medical device 100*a*, the processor 200 may set a safe movement path of the portable medical device 100*a* that moves away from the obstacle.

The processor 200 may control the portable medical device 100*a* to automatically move according to the set safe movement path. The processor 200 may control the drive motor 240 to control the speed and moving direction of the portable medical device 100*a*.

The processor 200 may also detect an obstacle above the portable medical device 100*a* based on signals detected by an ultrasonic sensor or a camera directed upwards from the portable medical device 100*a*. According to an embodiment, the processor 200 may set a safe movement path for avoiding the obstacle above the portable medical device 100*a*.

The processor 200 may control the drive motor 240 so that the portable medical device 100*a* decelerates or stops when the distance between the portable medical device 100*a* and the obstacle is smaller than or equal to a reference distance.

According to an embodiment, the display 300 may display the periphery image captured by the camera 210, information about the obstacle, and the expected movement path of the portable medical device 100*a*.

The information about the obstacle may include the position, size, and shape of the obstacle, the distance between the obstacle and the portable medical device 100*a*, expected time to collision, and collision probability, etc.

The display 300 may overlappingly display the information about the obstacle and the expected movement path on the periphery image.

The display 300 may display a reference line indicating the forward direction of the portable medical device 100*a*. The display 300 may display the expected movement path using one or more direction lines indicating the traveling direction of the portable medical device 100*a* generated from data from the torque sensor 230.

When collision with an obstacle is possible, the display 300 may display information about a safe movement path that avoids the obstacle.

Figure 3:
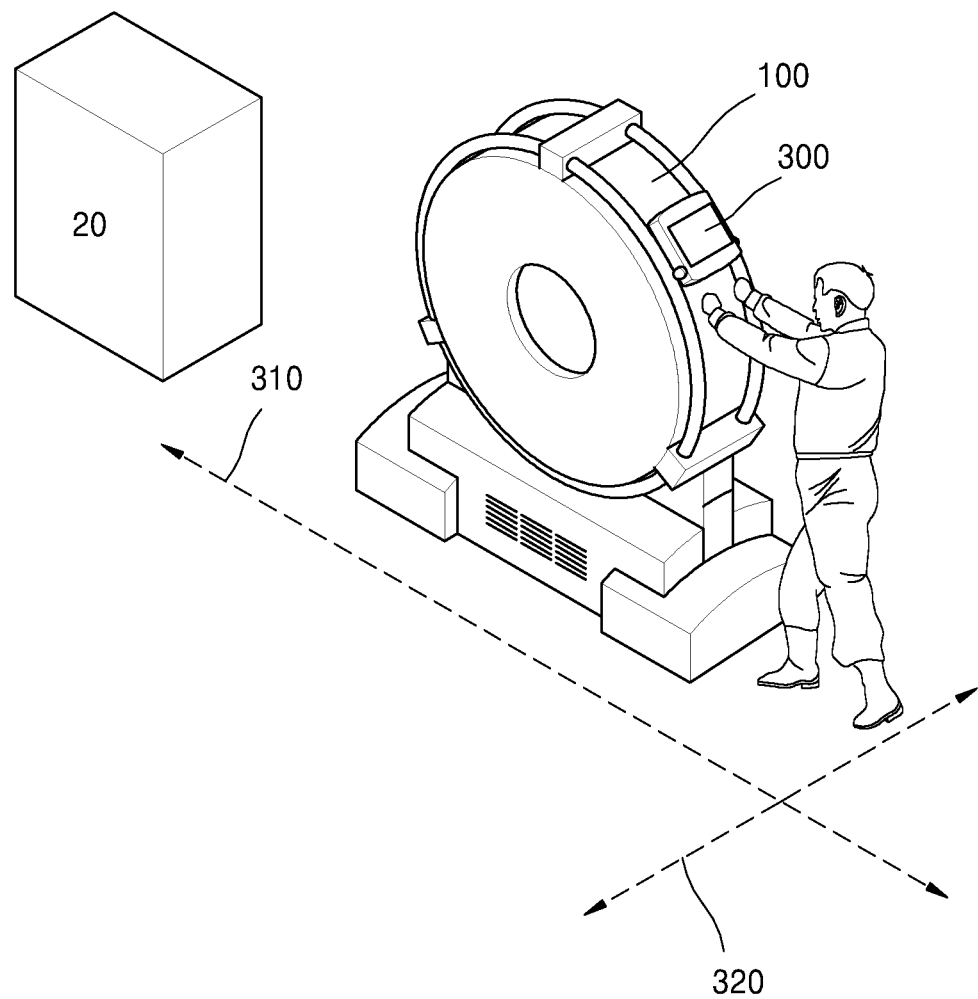
FIG. 3 is a perspective view illustrating an operation of the portable medical device according to an embodiment.

FIG. 3 is a perspective view illustrating an operation of a portable medical device 100 according to an embodiment.

The portable medical device 100 may have various degrees of freedom of movement. For example, the portable medical device 100 may move in one axial direction 310 or on two axial directions 310 and 320. The portable medical device 100 may be moved using an electrical motor according to user input entered in various input units such as a touch screen, a button, etc. Alternatively, the portable medical device 100 may be moved by a force applied by a user.

As shown, obstacle 20 may be in the way when the portable medical device 100 is moved in the axial direction 310.

According to an embodiment, the display 300 may display an expected movement path of the portable medical device 100 while the portable medical device 100 is moving.

The portable medical device 100 may display a periphery image of the portable medical device 100 captured by the camera 210 at a third person view point. The portable medical device 100 may display the periphery image in real time. The portable medical device 100 may display the periphery image and the expected movement path.

The portable medical device 100 may be moved by receiving power from a drive motor. As explained above, the portable medical device 100 may include a left wheel drive motor and a rear wheel drive motor. The portable medical device 100 may calculate the expected movement path of the portable medical device 100 by using a difference of torque values between the left wheel drive motor and the rear wheel drive motor. Alternatively, the portable medical device 100 may calculate the expected movement path of the portable medical device 100 by using a difference between the number of revolutions of the left wheel drive motor and the number of revolutions of the rear wheel drive motor.

Figure 4:
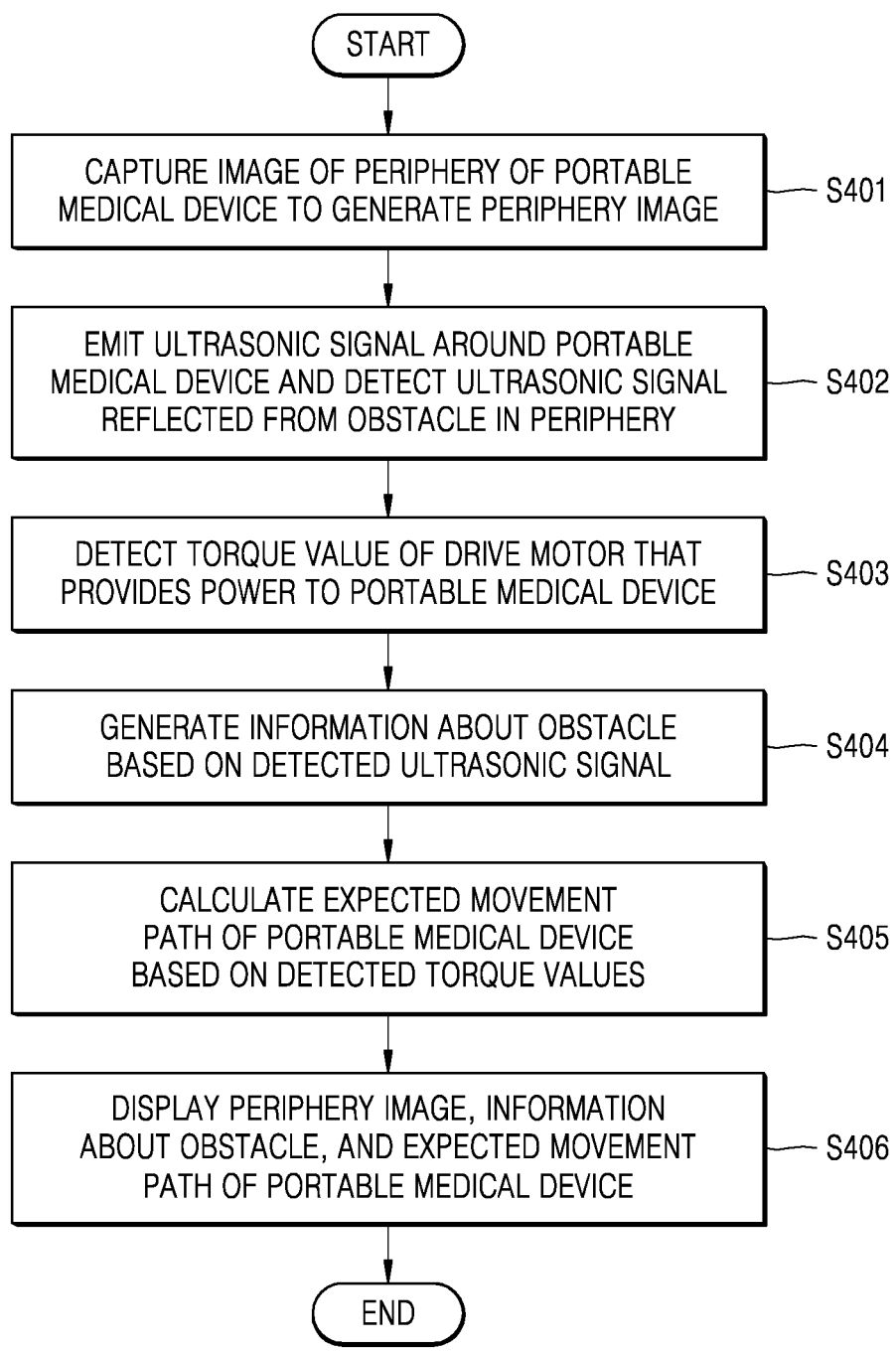
FIG. 4 is a flowchart illustrating a process for controlling an operation of a portable medical device, according to an embodiment.

FIG. 4 is a flowchart illustrating a process for controlling an operation of a portable medical device according to an embodiment.

According to an embodiment, in operation S401, the portable medical device may capture the periphery of the portable medical device to generate a periphery image. The portable medical device may acquire at least one image of the periphery of the portable medical device using at least one camera. The captured images may be captured at different points in time.

The portable medical device may combine the images to generate the periphery image of the portable medical device. The generated periphery image of the portable medical device may show the portable medical device at a third person view point.

In operation S402, the portable medical device may emit an ultrasonic signal around the portable medical device and detect the ultrasonic signal reflected from an obstacle of the periphery. The portable medical device may include at least one ultrasonic sensor. The portable medical device may detect the obstacle in the periphery of the portable medical device by using the at least one ultrasonic sensor. The portable medical device may detect static obstacles and moving obstacles.

In operation S403, the portable medical device may detect torque values of one or more drive motors that are used to move the portable medical device. The portable medical device may detect torque values of a left wheel drive motor and a right wheel drive motor.

In operation S404, the portable medical device may generate information about an obstacle based on the detected ultrasonic signal. The information about the obstacle may include presence of the obstacle, the position of the obstacle, the movement of the obstacle, the distance between the obstacle and the portable medical device, etc.

In operation S405, the portable medical device may calculate an expected movement path of the portable medical device based on the detected torque values. The portable medical device may determine a moving direction and a moving speed of the portable medical device from the difference in the torque values between the left wheel drive motor and the right wheel drive motor. The portable medical device may calculate the expected movement path of the portable medical device based on the determined movement direction and movement speed.

In operation S406, the portable medical device may display the periphery image, the information about the obstacle, and the expected movement path of the portable medical device.

According to an embodiment, the portable medical device may display the information about the obstacle and the expected movement path of the portable medical device by combining the information about the obstacle and the expected movement path with the periphery image. Information about the obstacle may be displayed when the obstacle is within a predetermined distance from the expected movement path. The portable medical device may display the periphery image in real time as the portable medical device moves along the expected movement path.

Figure 5:
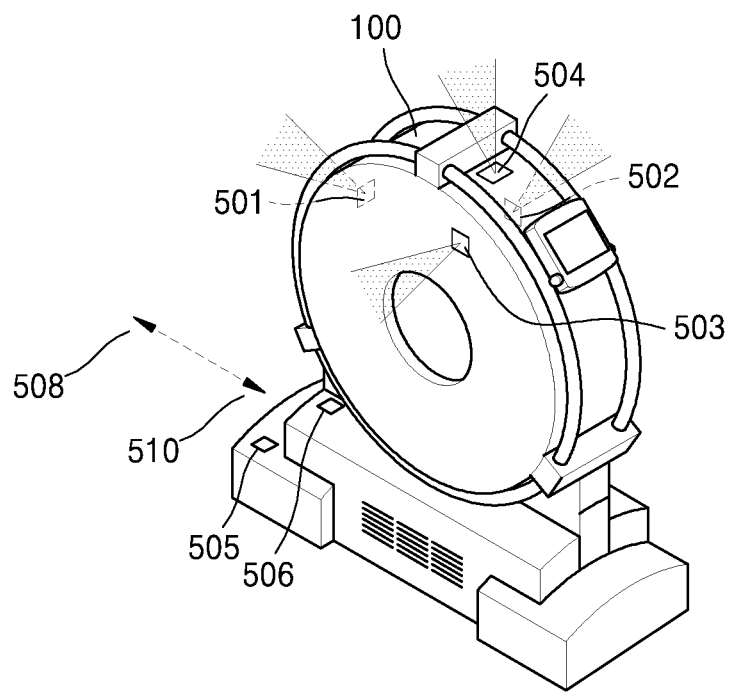
FIG. 5 is a perspective view illustrating a portable medical device equipped with cameras and ultrasonic sensors, according to an embodiment.

FIG. 5 is a perspective view illustrating the portable medical device 100 equipped with cameras 501, 502, 503, and 504 and ultrasonic sensors 505 and 506 according to an embodiment.

The portable medical device 100 according to an embodiment may include at least one camera or at least one ultrasonic sensor.

The portable medical device 100 according to an embodiment may include the first camera 501 that captures a forward view of the portable medical device 100 when the portable medical device 100 moves in that direction (e.g. the direction indicated by arrow 508), the second camera 502 that captures images at a right side, and the third camera 503 that captures images at a left side of the portable medical device 100.

The first camera 501 may be installed opposite the display 507. The first camera 501 may capture images of obstacles in the forward path of the portable medical device 100.

The second camera 502 may capture images of the right side of the portable medical device 100 in real time as the portable medical device 100 is moving. Thus, the second camera 502 may capture images of obstacles located on the right side of the portable medical device 100.

The third camera 503 may capture image of the left side of the portable medical device 100 in real time as the portable medical device 100 is moving. The third camera 503 may capture images of obstacles located on the left side of the portable medical device 100.

The portable medical device 100 may combine images received from the first camera 501, the second camera 502, and the third camera 503 to generate a periphery image. The periphery image may show the portable medical device 100 in its immediate environment from a third person view point.

According to an embodiment, the portable medical device 100 may change the viewpoint of the displayed image. For example, the portable medical device 100 may display images only from the first camera 501, thereby display images from the view point of the first camera 501. The portable medical device 100 may also enlarge a part of a periphery image selected by the user. The portable medical device 100 may store the periphery image as color representation information or coordinate information of a collection of image pixels according to a predetermined scheme, e.g. JPEG.

As explained above, the portable medical device 100 may generate the periphery image by combining images captured by a plurality of cameras. In addition, the portable medical device 100 may display only an image captured by any one camera among the plurality of cameras.

The portable medical device 100 may enlarge a portion of the image selected according to a user input. The user input may be an input via an input device such as a voice input or an input via a touch screen. The user may also select various displays of the images captured by the first camera 501, the second camera 502, and the third camera 503. For example, the user may enter an input for selecting any one of the plurality of cameras, for selecting a part of the periphery image to be enlarged, and for changing the viewpoint of the periphery image.

The portable medical device 100 may also include the fourth camera 504 directed upwards from the portable medical device 100. The portable medical device 100 may generate the periphery image using images captured by the fourth camera 504. This way, the portable medical device 100 may detect obstacles located above the portable medical device 100 using the fourth camera 504.

For example, when the portable medical device 100 moves through a hospital hallway, using the fourth camera 504, the portable medical device 100 may capture obstacles above the portable medical device 100 such as lamps or signs placed on the ceiling. The portable medical device 100 may notify the user of the obstacle by displaying information about the obstacles on the ceiling.

According to an embodiment, the portable medical device 100 may detect obstacles using at least one ultrasonic sensor. For example, the portable medical device 100 may include the two ultrasonic sensors 505 and 506 on the left and right sides of the portable medical device 100 when the portable medical device 100 is moving in the directions shown by arrows 508 and 510. The portable medical device 100 may detect obstacles within the range of the ultrasonic sensors 505 and 506 when ultrasonic waves are radiated by the ultrasonic sensors 505 and 506 and are reflected by the obstacles. The reflected waves may then be detected by the ultrasonic sensors 505 and 506.

Figure 6:
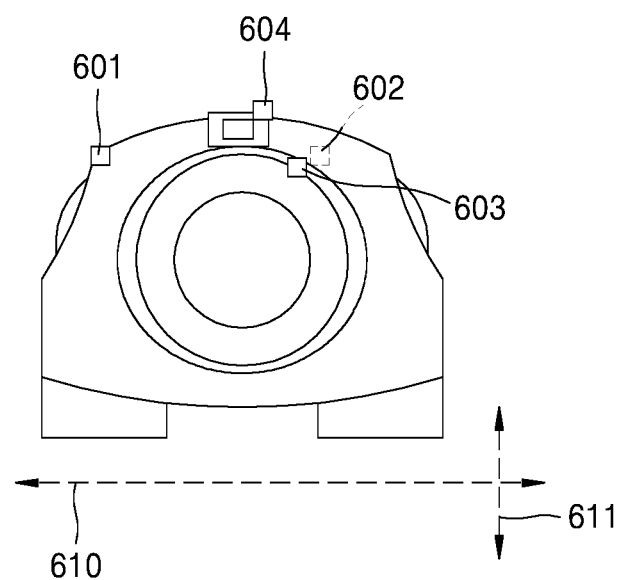
FIG. 6 is a plane view illustrating cameras and an ultrasonic sensor mounted on a CT system, according to an embodiment.

FIG. 6 is a plane view illustrating cameras 610, 602, 603, and 604 and an ultrasonic sensor mounted on a CT system according to an embodiment.

According to an embodiment, the CT system may move in the direction 610 from an operation room to another operation room. Components of the CT system, for example the gantry, may move in the direction 611 capture images of an object.

The CT system may include the first camera 601 that captures images at the front of the CT system as it moves in the direction 610, the second camera 602 that captures images at the right side, and the third camera 603 that captures images at the left side. In addition, according to an embodiment, the CT system may include the fourth camera 604 directed upwards from the CT system.

The CT system may generate a periphery image using at least one of images captured by the first camera 601, the second camera 602, the third camera 603, and the fourth camera 604.

The CT system may display the periphery image in real time. The CT system may display the periphery image so that the user of the CT system may observe the CT system from a third person view point.

Figure 7:
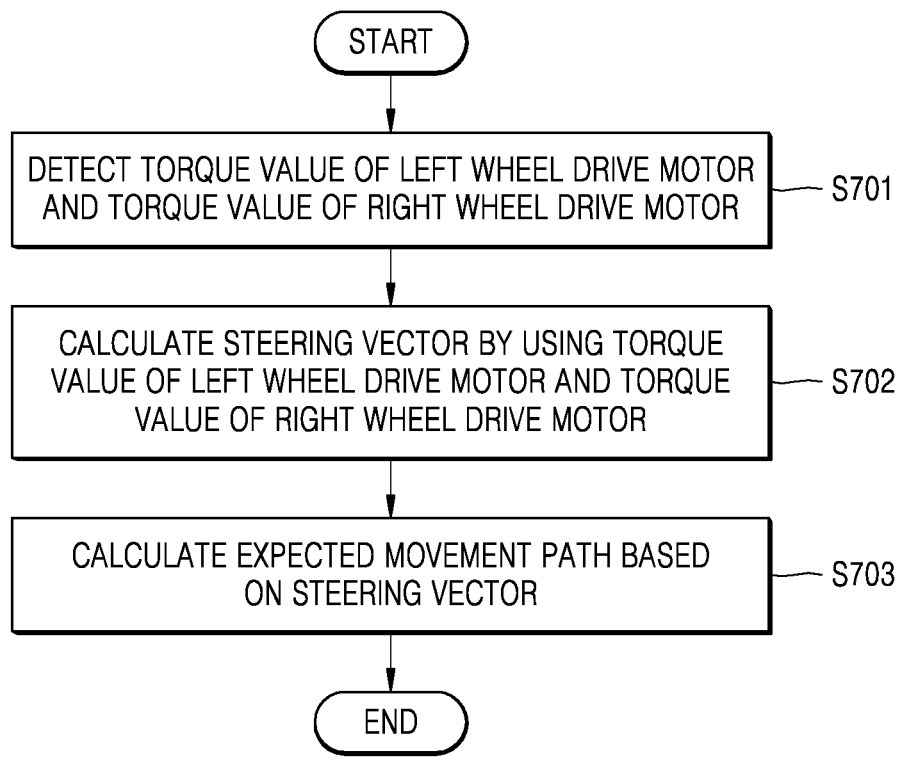
FIG. 7 is a flowchart illustrating a process of calculating a steering vector and calculating an expected movement path, according to an embodiment.

FIG. 7 is a flowchart illustrating a process of calculating a steering vector and calculating an expected movement path according to an embodiment.

According to an embodiment, in operation S701, a portable medical device may detect a torque value of a left wheel drive motor and a torque value of a right wheel drive motor.

The left wheel drive motor may provide power to the left wheel of the portable medical device. The right wheel drive motor may provide power to the right wheel of the portable medical device. The left wheel drive motor and the right wheel drive motor may be driven independently of each other.

The portable medical device may independently detect the torque values of the left wheel drive motor and the right wheel drive motor. The portable medical device may detect the torque values of the left wheel drive motor and the right wheel drive motor in real time.

In operation S702, the portable medical device may calculate the steering vector using the torque value of the left wheel drive motor and the torque value of the right wheel drive motor.

The portable medical device may calculate the steering vector in real time. The portable medical device may calculate a steering direction and a moving speed of the portable medical device by using the difference between the torque value of the left wheel drive motor and the torque value of the right wheel drive motor. The portable medical device may determine the steering vector based on the steering direction and the moving speed.

In operation S703, the portable medical device may calculate an expected movement path based on the steering vector.

For example, the portable medical device may expect a direction in which the portable medical device moves forward based on the current steering vector. The expected movement path calculated by the portable medical device may change as the steering vector changes.

Figure 8:
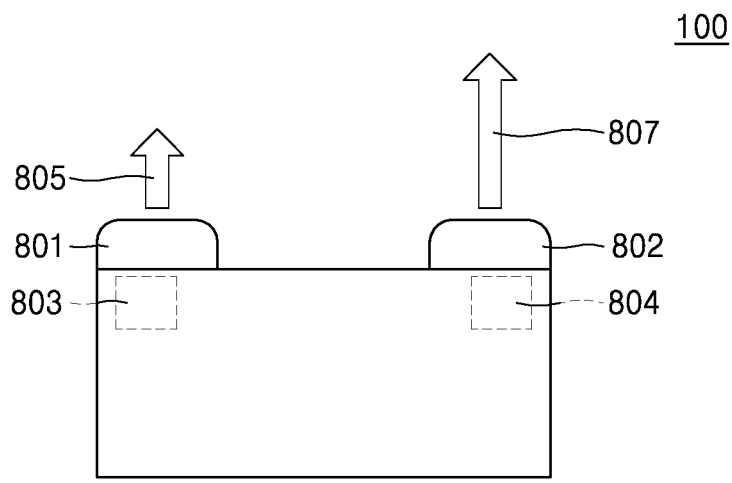
FIG. 8 is a block diagram illustrating a process of detecting torque values of a left wheel drive motor and a right wheel drive motor of a portable medical device, according to an embodiment.

FIG. 8 is a block diagram illustrating a process of detecting a torque value 805 of a left wheel drive motor 803 and a torque value 807 of a right wheel drive motor 804 of the portable medical device 100 according to an embodiment.

The portable medical device 100 may include at least one pair of wheels. The at least one pair of wheels may be a left wheel 801 and a right wheel 802. The left wheel 801 and the right wheel 802 may be connected to the portable medical device 100 by a 360 degree rotatable connector. Thus, the left wheel 801 and the right wheel 802 may a 360 degree range of motion.

According to an embodiment, the left wheel 801 may be powered by the left wheel drive motor 803. The right wheel 802 may be powered by the right wheel drive motor 804. The left wheel drive motor 803 and the right wheel drive motor 804 may independently supply power to their respective wheels.

The portable medical device 100 may detect the moving direction and the moving speed of the portable medical device 100 by comparing the torque value 805 of the left wheel drive motor 803 and the torque value 807 of a right wheel drive motor 804.

For example, the portable medical device 100 may determine that the expected movement path of the portable medical device 100 is "straight-ahead forward" when the torque value of the left wheel drive motor 803 and the torque value of the right wheel drive motor 804 are substantially the same.

As another example, as shown in FIG. 8, when the torque value 807 of the right wheel drive motor 804 is greater than the torque value 805 of the left wheel drive motor 803, the portable medical device 100 may be expected to turn to the left. Thus, the portable medical device 100 may calculate the expected movement path of the portable medical device 100 by determining the difference between the torque value 807 of the right wheel drive motor 804 and the torque value 805 of the left wheel drive motor 803.

Figure 9:
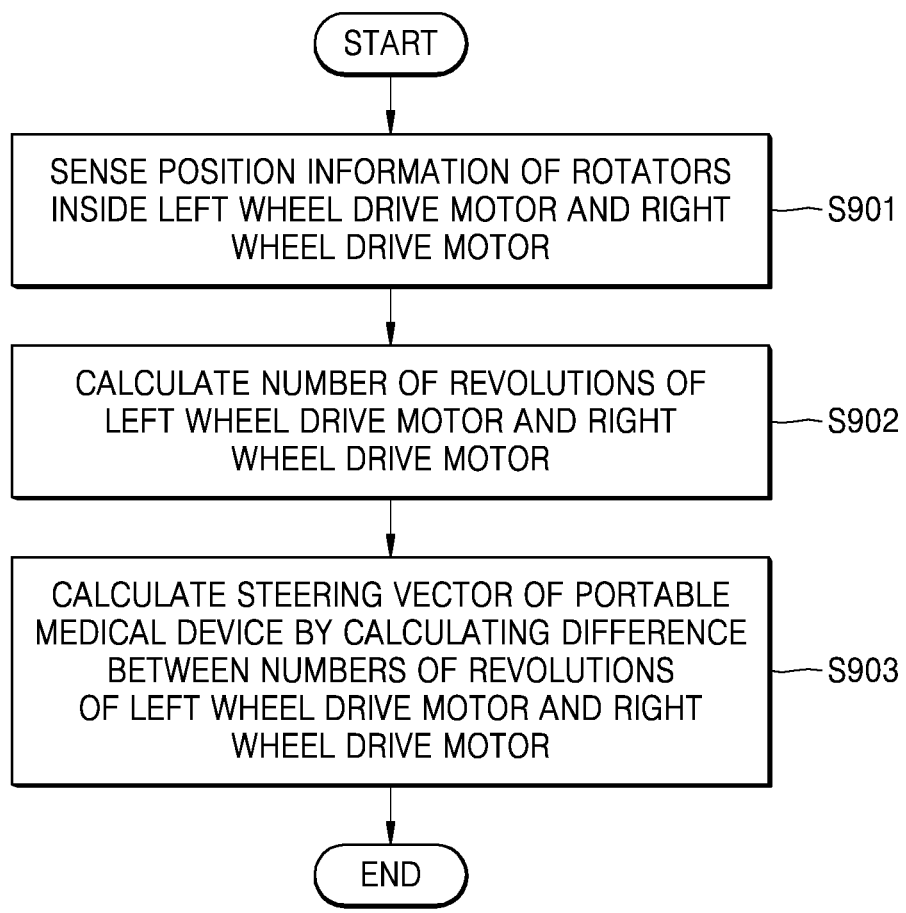
FIG. 9 is a flowchart illustrating a process of calculating a steering vector, according to an embodiment.

FIG. 9 is a flowchart illustrating a process of calculating a steering vector according to an embodiment.

According to an embodiment, in operation S901, a portable medical device may sense position information of rotators inside a left wheel drive motor and a right wheel drive motor. For example, the portable medical device may sense the position information of the rotor included in the left wheel drive motor. In addition, the portable medical device may sense the position information of the rotor included in the right wheel drive motor.

In operation S902, the portable medical device may calculate the number of revolutions of the left and right wheel drive motors using the position information of the rotors.

For example, the portable medical device may calculate the number of revolutions of the left wheel drive motor using the position information of the corresponding rotor. The portable medical device may calculate the number of revolutions of the right wheel drive motor by using the position information of the corresponding rotor.

In operation S903, the portable medical device may calculate the steering vector of the portable medical device by calculating the difference between the number of revolutions of the left wheel drive motor and the right wheel drive motor.

The portable medical device may calculate the different by comparing the number of revolutions of the left wheel drive motor and the number of revolutions of the right wheel drive motor. The portable medical device may determine a moving direction and a moving speed of the portable medical device according to the difference between the numbers of revolutions. The portable medical device may then calculate the steering vector based on the moving direction and the moving speed.

Figure 10:
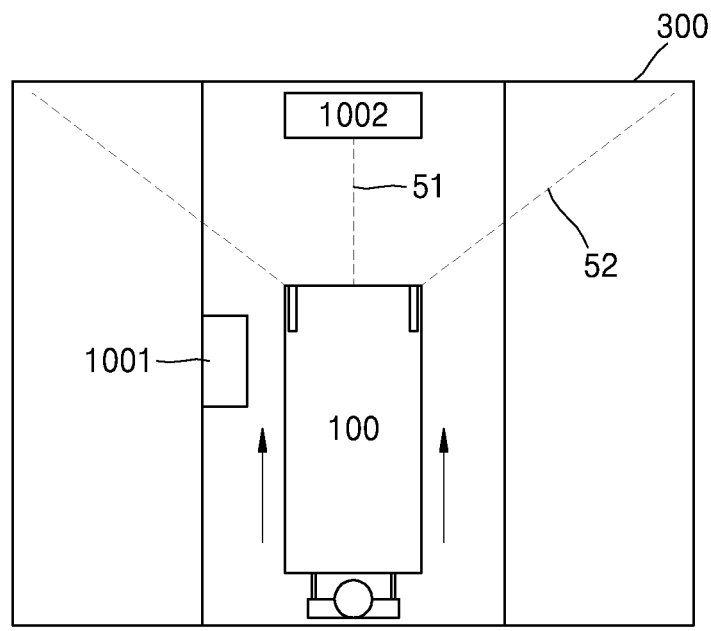
FIG. 10 is an exemplary display showing an expected movement path of a portable medical device, according to an embodiment.

FIG. 10 is an exemplary display of the display 300 showing an expected movement path of the portable medical device 100 according to an embodiment.

As shown in FIG. 10, the display 300 may display the expected movement path of the portable medical device 100. In this periphery image, the display 300 may display information about an obstacle and the expected movement path of the portable medical device.

The portable medical device 100 may display the periphery image of the portable medical device 100 from a third person view point on the display 300. Accordingly, the user view the periphery image to understand spatial relationships between the portable medical device 100 and any obstacles in the expected movement path of the portable medical device 100.

Referring to FIG. 10, the display 300 may display an obstacle 1002 in the expected movement path of the portable medical device 100 and an obstacle 1001 along the edge of the expected movement path. The display 300 may display the positions of the obstacles 1001 and 1002, the approximate sizes of the obstacles 1001 and 1002, and the approximate distance between the obstacles 1001 and 1002 and the portable medical device 100. Thus, even when the portable medical device 100 is obstructing the user's view, the user may be able to see the obstacles 1001 and 1002 by checking the display 300.

The display 300 may display a reference line 51 indicating the forward direction of the portable medical device 100. The display 300 may display the forward direction according to the current steering vector of the portable medical device 100. Thus, the user may be able to see the current moving direction of the portable medical device 100 in real time.

The portable medical device 100 may display the expected movement path using a direction line. As explained above, the expected movement path may be calculated from the detected torque values of the drive motors of the portable medical device 100. Here, the direction line for the expected movement path may be the same as the reference line 51 when the expected movement path is straight ahead. However, the direction line for the expected movement path may be displayed independently from the reference line 51 when the steering vector changes from straight ahead.

According to an embodiment, the portable medical device 100 may provide a guideline 52 according to a steering angle of the portable medical device 100.

The guideline 52 may indicate the range of motion available to the portable medical device 100. For example, the guideline 52 may be generated by taking into account the current movement direction and the range of possible steering vectors available to the portable medical device 100 at a particular point in time.

The guideline 52 may be changed when the steering vector of the portable medical device 100 changes. In addition, guidelines of the left wheel and the right wheel may be independently displayed.

Figure 11:
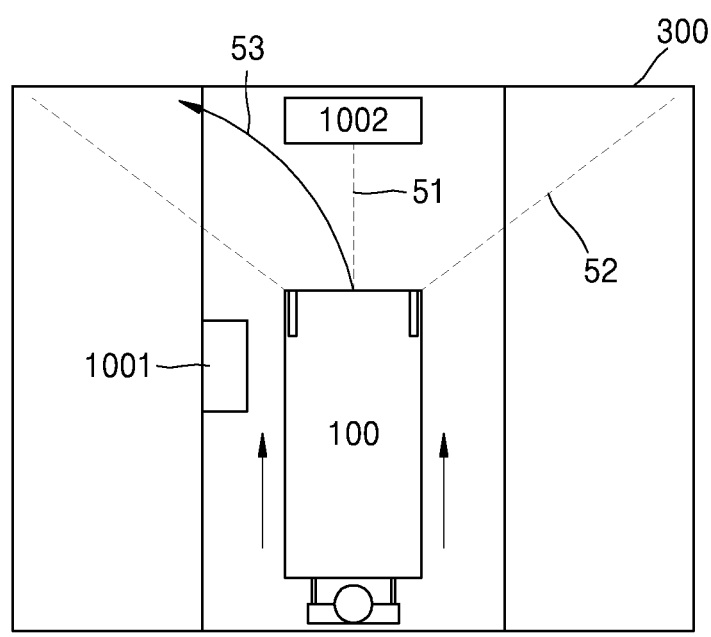
FIG. 11 is an exemplary display showing a safe movement path when obstacles are detected in an expected movement path of a portable medical device, according to an embodiment.

FIG. 11 is an exemplary display of the display 300 showing a safe movement path 53 when the obstacles 1001 and 1002 are detected in an expected movement path of the portable medical device 100 according to an embodiment.

When the obstacles 1001 and 1002 are located in the expected movement path of the portable medical device 100, the portable medical device 100 may set the safe movement path 53 so that the portable medical device may move away from the obstacles 1001 and 1002.

The display 300 may display the safe movement path 53 on the periphery image. The safe movement path 53 may be a movement path set in order for the portable medical device 100 to avoid the obstacles 1001 and 1002.

The safe movement path 53 according to an embodiment may be displayed as a direction line indicating a traveling direction of the portable medical device 100. In other embodiments, the safe movement path 53 may be displayed as a plurality of safe movement paths.

According to one embodiment, the user may avoid the obstacle 1002 by moving the portable medical device 100 along the safe movement path 53 displayed on the display 300.

In another embodiment, the portable medical device 100 may automatically control its drive motor so that the portable medical device 100 is automatically move according to the set safe movement path 53. In doing so, the portable medical device 100 may control its drive motor so that its steering vector is changed in accordance with the safe movement path 53.

Figure 12:
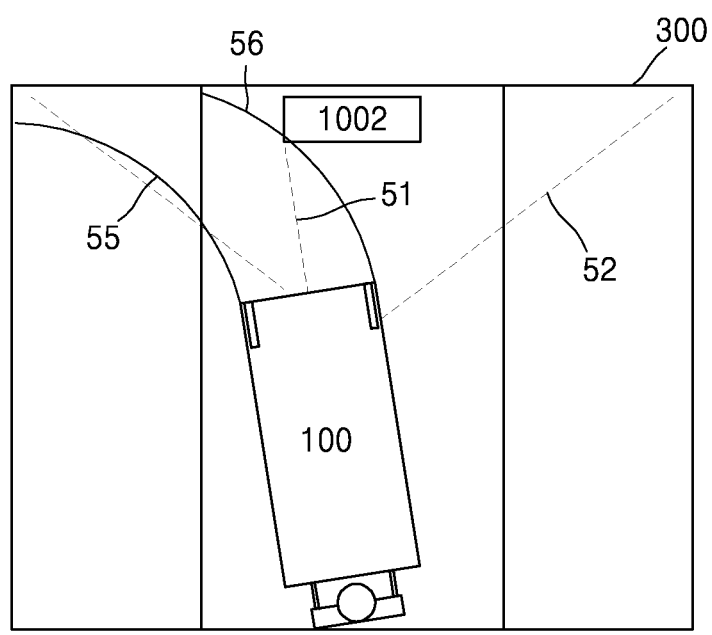
FIG. 12 is an exemplary display showing changes to an expected movement path and a guideline when a portable medical device changes a moving direction, according to an embodiment.

FIG. 12 is an exemplary display of the display 300 showing changes to an expected movement path and guideline 52 when the portable medical device 100 changes a moving direction according to an embodiment.

When the portable medical device 100 changes the moving direction to move to a path for avoiding the obstacle 1001, the display 300 may display estimated movement paths 55 and 56 based on the real-time movement direction of the portable medical device 100 for assisting the movement of the portable medical device 100. According to an embodiment, the estimated movement paths 55 and 56 may be displayed as the movement path 55 of the left wheel and the movement path 56 of the right wheel. The movement path 55 and the movement path 56 may be independently displayed according to the number of revolutions, torque values, and steering input values of the left wheel drive motor and the right wheel drive motor of the portable medical device 100, respectively.

According to an embodiment, the user may refer to the movement paths 55 and 56 to confirm the real-time movement of the portable medical device 100. In addition, the user may also use the movement paths 55 and 56 to guide the movement of the portable medical device 100.

Further, as the portable medical device 100 moves, the steering vector and the steering angle of the portable medical device 100 also change. The portable medical device 100 may change the guideline 52 based on the changed steering vector and steering angle and display the guideline 52 on a screen of the display 300.

Figure 13:
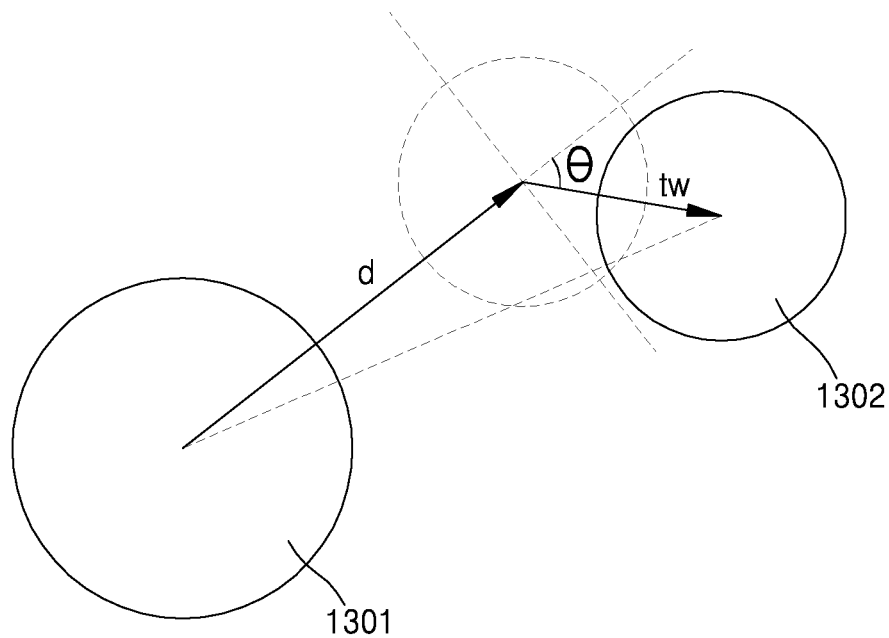
FIG. 13 and FIG. 14 are diagrams illustrating a process of determining a possibility of collision between portable medical devices and moving obstacles, according to an embodiment.
Figure 14:
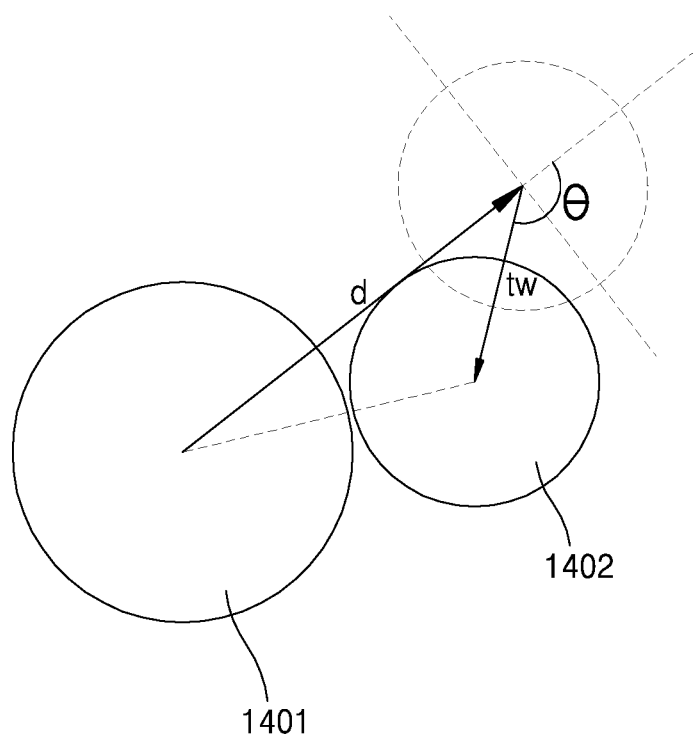

FIGS. 13 and 14 are diagrams illustrating a process of determining a possibility of collision between portable medical devices 1301 and 1401 and moving obstacles 1302 and 1402, respectively, according to an embodiment.

According to an embodiment, a portable medical device may determine whether collision with an obstacle is possible by using the relative position [d=(a, b)−(0,0)] and the relative speed [w=(ux−vx, uy−Vy)] of a moving obstacle with respect to the portable medical device.

The portable medical device may set the safe movement path based on whether collision is possible.

FIG. 13 is a diagram illustrating a process for determining that collision between the portable medical device 1301 and the moving obstacle 1302 is not possible, according to an embodiment.

According to this embodiment, a vector d is a relative position vector indicating the relative position between the portable medical device 1301 and the moving obstacle 1302. A vector tw is a relative velocity vector representing the relative velocity between the portable medical device 1301 and the moving obstacle 1302.

When magnitude of angle θ formed by the relative position vector d and the relative velocity vector tw is between 0 and 90 degrees, the portable medical device 1301 may determine that collision between the portable medical device 1301 and the moving obstacle 1302 is not possible. As shown in FIG. 13, the distance between the portable medical device 1301 and the moving obstacle 1302 may not decrease.

FIG. 14 is a diagram illustrating a process of determining that that collision between the portable medical device 1401 and the moving obstacle 1402 is possible, according to an embodiment.

When the magnitude of the angle θ formed by the relative position vector d and the relative velocity vector tw is between 90 and 180 degrees, the portable medical device 1401 may determine a distance between the portable medical device 1401 and the moving obstacle 1402. The portable medical device 1401 may determine that collision is possible if the distance between the portable medical device 1401 and the moving obstacle 1402 is smaller than the sum of radiuses of the portable medical device 1401 and the moving obstacle 1402.

As shown in FIG. 14, as the portable medical device 1401 and/or the moving obstacles 1402 moves, the distance between the portable medical device 1401 and the moving obstacles 1402 decreases. The portable medical device 1401 may set a safe movement path to avoid the moving obstacle 1402 after determining that a collision between the portable medical device 1401 and the moving obstacle 1402 is possible.

Figure 15:
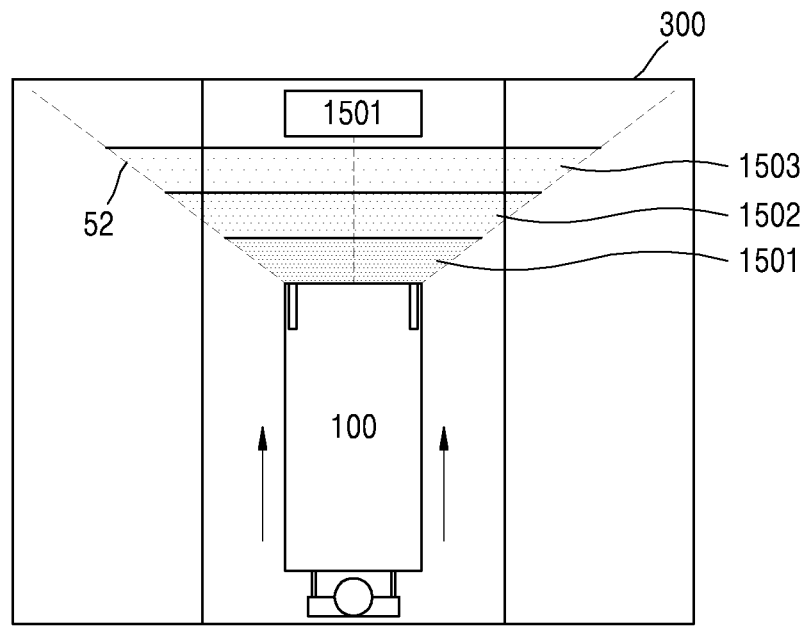
FIG. 15 is a view showing a user interface (UI) that changes as a distance between a portable medical device and an obstacle decreases, according to the embodiment.

FIG. 15 is a view showing a user interface (UI) that changes as a distance between the portable medical device 100 and the obstacle 1002 decreases, according to the embodiment.

The portable medical device 100 may change the display of information on the display 300 as the portable medical device 100 approaches the obstacle 1002.

For example, the portable medical device 100 may change the colors of the sections 1501, 1502, and 1503 as the portable medical device 100 approaches the obstacle 1002.

Also, as the portable medical device 100 approaches the obstacle 1002, the portable medical device 100 may change the color of the obstacle 1002 itself or display a warning message. For example, the portable medical device 100 may display the obstacle 1002 to flash on the screen as the portable medical device 100 approaches the obstacle 1002. Alternatively, the portable medical device 100 may change the color of the obstacle 1002. Alternatively, the portable medical device 100 may display only an image acquired by a camera that captures the obstacle 1002. Alternatively, the portable medical device 100 may enlarge and display an image between the obstacle 1002 and the portable medical device 100.

According to another embodiment, the portable medical device 100 may change at least one of the shape, the width, the form, and the format of the guideline 52 displayed as the portable medical device 100 approaches the obstacle 1002.

According to yet another embodiment, the portable medical device 100 may output an alarm notification when the obstacle 1002 is located within a predetermined distance of the portable medical device 100. The alarm notification may be a visual alarm, an audible alarm, a tactile alarm, etc., or may be a combination thereof.

Figure 16:
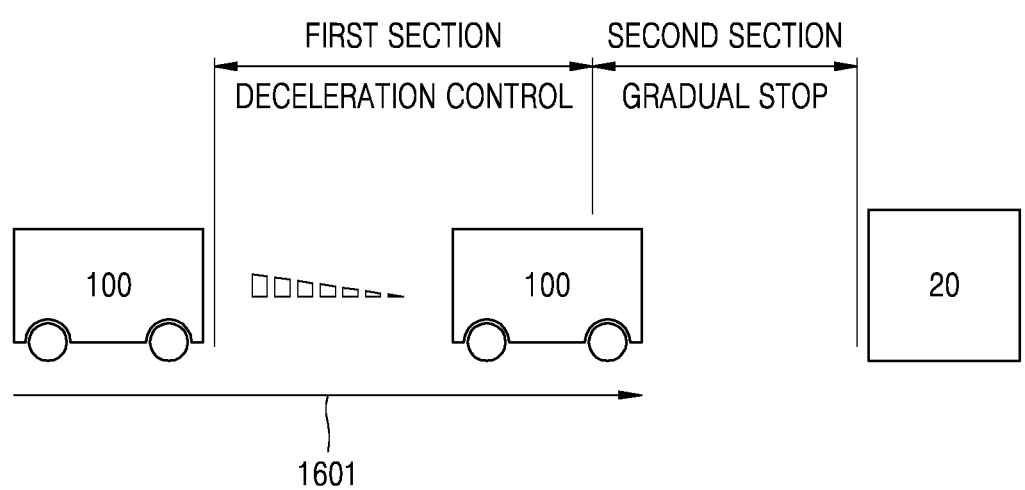
FIG. 16 is a diagram illustrating a process of controlling a portable medical device as the portable medical device approaches an obstacle, according to an embodiment.

FIG. 16 is a diagram illustrating a process of controlling a portable medical device as the portable medical device 100 approaches an obstacle 20 according to an embodiment.

As shown in FIG. 16, the obstacle 20 may be positioned in the moving direction 1601 of the portable medical device 100. According to an embodiment, the user may not have sufficient time to react to the obstacle. Accordingly, a method of automatically controlling the portable medical device 100 will be described.

According to an embodiment, when the distance between the portable medical device 100 and the obstacle 20 is less than or equal to a reference distance, the portable medical device 100 may control its drive motor to decelerate or stop the portable medical device 100.

As shown in FIG. 16, the portable medical device 100 may set a first section of distance from the obstacle 20 and a second section of distance from the obstacle 20. The number of sections and the lengths of the sections may be arbitrarily set and may be set by the user.

In one example, when the portable medical device 100 is positioned in the first section, the portable medical device 100 may control the portable medical device 100 to decelerate. Alternatively, according to another embodiment, the portable medical device 100 may control the direction of the portable medical device 100 to change.

When the portable medical device 100 is positioned in the second section, the portable medical device 100 may control the portable medical device 100 to stop gradually. As a result, collision with the obstacle 20 may be avoided.

Figure 17:
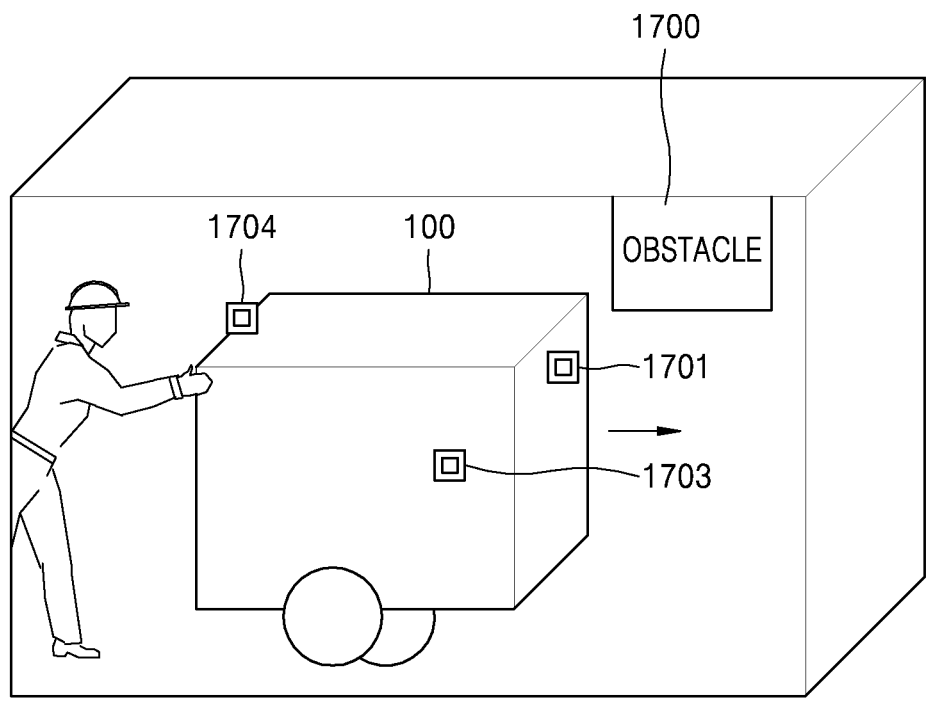
FIG. 17 is a perspective view illustrating a process for avoiding an obstacle located above a portable medical device, according to an embodiment.

FIG. 17 is a perspective view illustrating a process for avoiding an obstacle 1700 located above the portable medical device 100 according to an embodiment.

As shown in FIG. 17, since the portable medical device 100 may be mostly moved within hospitals, there is a possibility that the portable medical device 100 may collide with the obstacle 1700 mounted on the ceilings of the corridors in the hospitals. The portable medical device 100 may include a fourth camera 1704 mounted upwards from the portable medical device 100 that captures images of the ceilings in order to detect the obstacle 1700.

The portable medical device 100 may also include an upper ultrasonic sensor (not shown) that emits an ultrasonic signal upwards and detects the ultrasonic signal reflected from obstacles mounted on the ceiling. The portable medical device 100 may detect the obstacle 1700 based on the ultrasonic signal detected by the upper ultrasonic sensor.

The portable medical device 100 may generate the periphery image by adding images received from a fourth camera 1704 to images received from a first camera 1701 that captures images at the front of portable medical device 100, a second camera (not shown) that captures images at the right side, and a third camera 1703 that captures images at the left side.

According to another embodiment, the portable medical device 100 may display only the image received from the fourth camera 1704 in order to show the obstacle 1700 in detail on the display. The portable medical device 100 may display information about the obstacle 1700. The information about the obstacle 1700 may include the position, size, and shape of the obstacle 1700, whether collision with the obstacle 1700 is possible, the distance between the portable medical device 100 and the obstacle 1700, expected time to collision, etc.

Figure 18:
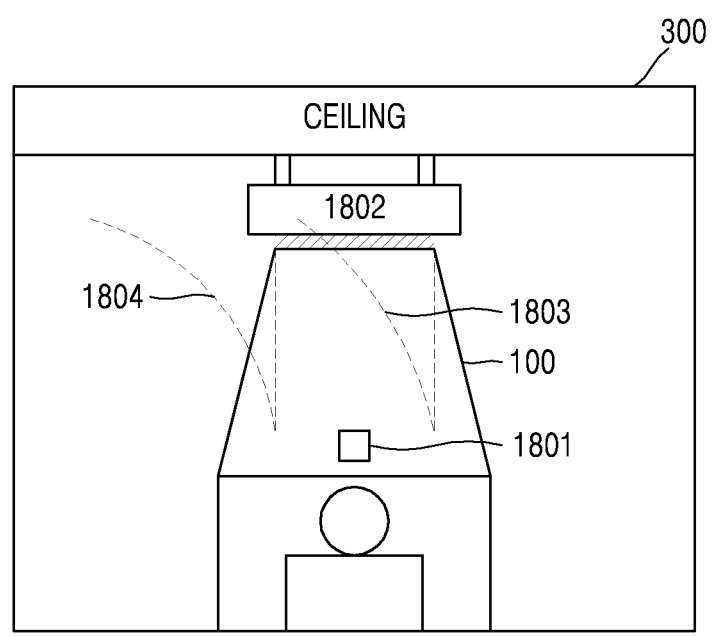
FIG. 18 is an exemplary display showing safe movement paths when an obstacle is located above a portable medical device, according to an embodiment.

FIG. 18 is an exemplary display on the display 300 showing safe movement paths 1803 and 1804 when an obstacle 1802 is located above the portable medical device 100 according to an embodiment.

The portable medical device 100 may acquire information about the obstacle 1802 mounted on the ceiling through a camera 1801 mounted on the top surface of the portable medical device 100. The portable medical device 100 may set the safe movement paths 1803 and 1804 for avoiding the obstacle 1802 based on torque values and rotation speeds of the left and right wheel drive motors of the portable medical device 100. The safe movement paths 1803 and 1804 may also be set by a steering input of a user.

The portable medical device 100 may display the safe movement paths 1803 and 1804 on the display 300. The portable medical device 100 may display the safe movement path 1804 of the left wheel and the safe movement path 1803 of the right wheel.

According to another embodiment, the portable medical device 100 may display currently expected movement path based on the steering vector of the portable medical device 100 together with the safe movement path. The portable medical device 100 may independently display the expected movement path and the safe movement path.

The embodiments disclosed herein may be implemented using computer-readable recording medium for storing instructions and data executable by a computer. The instructions may be stored in the form of program code, and when executed by the processor, may perform predetermined operations. Therefore, the instructions, when executed by a processor, may perform certain operations of the disclosed embodiments.

According to the disclosed embodiments, images showing the movements of a portable medical device from a third person view point is provided. This allows a user or operator of the portable medical device to better see the surrounding of the portable medical device while the portable medical device is being moved.

Further, according to the disclosed embodiments, collision with obstacles on the movement path of the portable medical device may be avoided.

Further, according to the disclosed embodiments, guides indicating the expected movement path of the portable medical device may be provided to the user, thereby improving user experience.

Further, according to the disclosed embodiments, an expected movement path based on torque values of the left and right wheel drive motors and a safe movement path for avoiding collisions may be provided. Therefore, an optimal movement path may be provided depending on the driving state of the portable medical device and the presence or absence of obstacles in the moving direction.

It should be understood that embodiments described herein are for illustrative purposes only and should not limit the disclosure. Descriptions of features or aspects within each embodiment should typically be considered as available for other similar features or aspects in other embodiments.

Aspects of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

While one or more embodiments have been described with reference to the figures, it will be understood by those of ordinary skill in the art that various changes in form and details may be made therein without departing from the spirit and scope as defined by the following claims.

What is claimed is:

1. A portable medical device comprising:
   a drive motor configured to provide power to move the portable medical device;
   at least one camera configured to capture an image of a periphery of the portable medical device;
   an ultrasonic sensor configured to emit an ultrasonic signal to the periphery of the portable medical device and detect the ultrasonic signal reflected from a first obstacle located in the periphery of the portable medical device;
   a torque sensor configured to detect a torque value of the drive motor;
   a processor configured to generate information about the first obstacle based on the image captured by the at least one camera and/or the detected ultrasonic signal, and calculate an expected movement path of the portable medical device based on the torque value detected by the torque sensor; and
   a display configured to display a periphery image using the image captured by the at least one camera, the information about the first obstacle, and the expected movement path of the portable medical device, wherein the drive motor comprises a left wheel drive motor and a right wheel drive motor, wherein the torque sensor is further configured to detect a torque value of the left wheel drive motor and a torque value of the right wheel drive motor, and wherein the processor is further configured to calculate a steering vector using the torque value of the left wheel drive motor and the torque value of the right wheel drive motor, and calculate the expected movement path based on the steering vector.

2. The portable medical device of claim 1, wherein the processor is further configured to:
- calculate a first number of revolutions of the left wheel drive motor and a second number of revolutions of the right wheel drive motor using position information of rotors inside the left wheel drive motor and the right wheel drive motor,
- compute a difference between the first number and the second number, and
- calculate the steering vector of the portable medical device based on the difference.

3. The portable medical device of claim 1, wherein the display is further configured to display the information about the first obstacle and the expected movement path on the periphery image.

4. The portable medical device of claim 3, wherein the display is further configured to display the expected movement path by using a reference line indicating a forward direction of the portable medical device and a direction line indicating an expected traveling direction of the portable medical device.

5. The portable medical device of claim 1, wherein the processor is further configured to set a safe movement path of the portable medical device for avoiding the first obstacle when the first obstacle is located within the expected movement path of the portable medical device, and
wherein the display is further configured to display information about the safe movement path.

6. The portable medical device of claim 5, wherein the processor is further configured to control the portable medical device to automatically move along the safe movement path.

7. The portable medical device of claim 5, wherein:
when the first obstacle is a moving obstacle, if a magnitude of an angle between a relative position vector, indicating a relative position between the portable medical device and the moving obstacle, and a relative velocity vector, indicating a relative velocity between the portable medical device and the moving obstacle, is between 0 degrees and 90 degrees, the processor is further configured to determine that collision between the portable medical device and the moving obstacle is not possible, and
if the magnitude of the angle is between 90 degrees and 180 degrees, and when a distance between the portable medical device and the moving obstacle is smaller than a sum of radiuses of the portable medical device and the moving obstacle, the processor is further configured to determine that the collision between the portable medical device and the moving obstacle is possible.

8. The portable medical device of claim 1, wherein the processor is further configured to output an alarm notification when the first obstacle is located within a predetermined range from the portable medical device, and wherein the alarm notification comprises at least one of a visual alarm, an audible alarm, and a tactile alarm.

9. The portable medical device of claim 1, wherein the processor is further configured to control the drive motor to decelerate or stop the portable medical device when a distance between the portable medical device and the first obstacle is smaller than or equal to a reference distance.

10. The portable medical device of claim 1, wherein the at least one camera comprises a first camera that captures images at a front of the portable medical device, a second camera that captures images at a right side of the portable medical device, and a third camera that captures images at a left side of the portable medical device, and wherein the processor is further configured to generate the periphery image by using images captured by the first, second, and third cameras.

11. The portable medical device of claim 10, wherein the at least one camera comprises a fourth camera directed upwards from the portable medical device,
wherein the ultrasonic sensor comprises an upper ultrasonic sensor configured to emit an ultrasonic signal upwards from the portable medical device and detect the ultrasonic signal reflected from a second obstacle located above the portable medical device,
wherein the processor is further configured to detect the second obstacle based on one or more images captured by the fourth camera and/or the ultrasonic signal detected by the upper ultrasonic sensor, and
wherein the display is further configured to display information about the second obstacle.

12. The portable medical device of claim 10, wherein the display is further configured to enlarge and display a selected part of the periphery image according to a user input that selects the part of the periphery image.

13. The portable medical device of claim 1, further comprising:
a user inputter configured to receive a steering input from a user,
wherein the processor is further configured to calculate the expected movement path of the portable medical device based on the steering input.

14. A method of controlling a portable medical device, the method comprising:
capturing an image of a periphery of the portable medical device to generate a periphery image;
emitting an ultrasonic signal to the periphery of the portable medical device;
detecting the ultrasonic signal reflected from an obstacle located in the periphery of the portable medical device;
detecting a torque value of a drive motor that provides power to move the portable medical device;
generating information about the obstacle based on the captured image and/or the detected ultrasonic signal;
calculating an expected movement path of the portable medical device based on the detected torque value; and
displaying the periphery image, the information about the obstacle, and the expected movement path of the portable medical device,
wherein the detecting of the torque value of the drive motor further comprises detecting a torque value of a left wheel drive motor of the drive motor and a torque value of a right wheel drive motor of the drive motor, and
wherein the calculating of the expected movement path of the portable medical device further comprises:

calculating a steering vector using the torque value of the left wheel drive motor and the torque value of the right wheel drive motor, and calculating the expected movement path based on the steering vector.

15. The method of claim 14, wherein the calculating of the steering vector further comprises:

calculating a first number of revolutions of the left wheel drive motor and a second number of revolutions of the right wheel drive motor using position information of rotors inside the left wheel drive motor and the right wheel drive motor, computing a difference between the first number and the second number, and calculating the steering vector of the portable medical device based on the difference.

16. The method of claim 14, wherein the displaying of the expected movement path of the portable medical device comprises displaying the information about the obstacle and the expected movement path on the periphery image.

17. The method of claim 14, further comprising:

setting a safe movement path of the portable medical device for avoiding the obstacle when the obstacle is located within the expected movement path of the portable medical device; and displaying information about the safe movement path.

18. A non-transitory computer-readable recording medium having recorded thereon a program for executing a method of controlling a portable medical device, wherein the method comprises:

capturing an image of a periphery of the portable medical device to generate a periphery image;

emitting an ultrasonic signal to the periphery of the portable medical device;

detecting the ultrasonic signal reflected from an obstacle located in the periphery of the portable medical device;

detecting a torque value of a drive motor that provides power to move the portable medical device;

generating information about the obstacle based on the captured image and/or the detected ultrasonic signal;

calculating an expected movement path of the portable medical device based on the detected torque value; and displaying the periphery image, the information about the obstacle, and the expected movement path of the portable medical device, wherein the detecting of the torque value of the drive motor further comprises detecting a torque value of a left wheel drive motor of the drive motor and a torque value of a right wheel drive motor of the drive motor, and wherein the calculating of the expected movement path of the portable medical device further comprises:

calculating a steering vector using the torque value of the left wheel drive motor and the torque value of the right wheel drive motor, and calculating the expected movement path based on the steering vector.

\* \* \* \* \*